US012788916B2

(12) United States Patent
Kremeier

(10) Patent No.: US 12,788,916 B2
(45) Date of Patent: Nov. 10, 2026

(54) METHOD FOR OPERATING A VENTILATOR FOR ARTIFICIAL VENTILATION OF A PATIENT, AND SUCH A VENTILATOR

(71) Applicant: Loewenstein Medical Technology S.A., Luxembourg (LU)

(72) Inventor: Peter Kremeier, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 618 days.

(21) Appl. No.: 17/167,193

(22) Filed: Feb. 4, 2021

(65) Prior Publication Data

US 2021/0244900 A1 Aug. 12, 2021

(30) Foreign Application Priority Data

Feb. 6, 2020 (DE) ......................... 102020103094.0

(51) Int. Cl.
*A61M 16/00* (2006.01)
*A61B 5/08* (2006.01)
(Continued)

(52) U.S. Cl.
CPC ......... *A61M 16/024* (2017.08); *A61B 5/0816* (2013.01); *A61B 5/0836* (2013.01);
(Continued)

(58) Field of Classification Search
CPC ............ A61M 16/0057; A61M 16/022; A61M 16/024; A61M 16/026; A61M 2230/40;
(Continued)

(56) References Cited

U.S. PATENT DOCUMENTS

| | | | | |
|---|---|---|---|---|
| 4,986,268 A * | 1/1991 | Tehrani | ................. | A61M 16/00 128/204.22 |
| RE40,402 E * | 6/2008 | Leonhardt | ................ | A62B 7/00 128/204.23 |

(Continued)

FOREIGN PATENT DOCUMENTS

| | | | |
|---|---|---|---|
| WO | 2005092415 A1 | 10/2005 | |
| WO | 2013163735 A1 | 11/2013 | |

OTHER PUBLICATIONS

Peyton et al., "Noninvasive measurement of intrapulmonary shunting," Journal of Cardiothoracic and Vascular Anesthesia, vol. 18, Issue 1, 2004, pp. 47-52, ISSN 1053-0770, https://doi.org/10.1053/j.jvca.2003.10.010.*

*Primary Examiner* — Joseph D. Boecker
(74) *Attorney, Agent, or Firm* — Abel Schillinger LLP

(57) ABSTRACT

A method for operating a ventilator for artificial ventilation of a patient, comprising: initial recording of at least one patient-specific physiological parameter, initial setting of at least one technical respiration parameter, and ventilation of the patient based on the technical respiration parameter. The technical respiration parameter corresponds to at least one of respiratory minute volume (VE), tidal volume ($V_T$), respiratory rate (RR), positive end-expiratory pressure (PEEP), or inspiratory oxygen concentration ($FiO_2$) made available by the ventilator. A repeating measurement of the parameter is carried out by the ventilator at time intervals, and an adaptation of the parameter is effected by the ventilator based on said repeating measurement. A ventilator for artificial ventilation of a patient is also proposed.

14 Claims, 5 Drawing Sheets

(51) Int. Cl.
*A61B 5/083* (2006.01)
*A61B 5/091* (2006.01)
*A61B 5/145* (2006.01)

(52) U.S. Cl.
CPC .......... *A61B 5/091* (2013.01); *A61B 5/14542* (2013.01); *A61M 16/0057* (2013.01); *A61M 16/0051* (2013.01); *A61M 2205/18* (2013.01); *A61M 2230/42* (2013.01); *A61M 2230/432* (2013.01); *A61M 2230/435* (2013.01); *A61M 2230/46* (2013.01)

(58) Field of Classification Search
CPC ........ A61M 2230/42; A61M 2230/432; A61M 2230/435; A61B 5/0816; A61B 5/0836; A61B 5/091; A61B 5/14542; A61B 5/14551
See application file for complete search history.

(56) References Cited

U.S. PATENT DOCUMENTS

2003/0111078 A1* 6/2003 Habashi .............. A61M 16/024 128/204.18
2005/0109340 A1* 5/2005 Tehrani .............. A61M 16/026 128/204.23
2007/0068528 A1 3/2007 Bohm et al.
2007/0163584 A1 7/2007 Boehm et al.
2008/0202525 A1* 8/2008 Mitton ................ A61M 16/104 128/204.22
2008/0202527 A1* 8/2008 Hutchinson ....... A61M 16/0051 128/204.23
2008/0236582 A1* 10/2008 Tehrani .............. A61M 16/024 128/204.22
2008/0295839 A1* 12/2008 Habashi ........... A61M 16/0051 128/204.22
2008/0314385 A1* 12/2008 Brunner ............. A61M 16/024 128/204.23
2009/0320836 A1* 12/2009 Baker, Jr. ............. A61M 16/12 128/203.14
2011/0023878 A1* 2/2011 Thiessen ............ A61M 16/024 128/204.23
2012/0145152 A1 6/2012 Lain et al.
2015/0034082 A1* 2/2015 Kimm ................ A61B 5/14542 128/202.16
2015/0114394 A1 4/2015 Klein et al.
2015/0231351 A1* 8/2015 Jonson ................ A61M 16/085 128/204.22
2018/0272087 A1* 9/2018 Von Blumenthal .......................... A61M 16/104
2020/0016350 A1* 1/2020 Heinonen .............. G16H 50/70
2020/0016352 A1* 1/2020 Stender ................ A61B 5/6823

* cited by examiner

METHOD FOR OPERATING A VENTILATOR FOR ARTIFICIAL VENTILATION OF A PATIENT, AND SUCH A VENTILATOR

CROSS-REFERENCE TO RELATED APPLICATIONS

The present application claims priority under 35 U.S.C. § 119 of German Patent Application No. 102020103094.0, filed Feb. 6, 2020, the entire disclosure of which is expressly incorporated by reference herein.

BACKGROUND OF THE INVENTION

1. Field of the Invention

The present invention relates to a method for operating a ventilator for artificial ventilation of a patient, with the following steps: initial recording of at least one patient-specific physiological parameter, initial setting of at least one technical respiration parameter, and ventilation of the patient on the basis of the technical respiration parameter. The invention further relates to a ventilator for artificial ventilation of a patient, preferably configured to be operated by an aforementioned method.

2. Discussion of Background Information

In machine ventilation of patients by means of a ventilator, respiratory gas is supplied at a positive pressure to the patient. For this reason, the airway pressure or alveolar pressure, at least during the inspiration phase of breathing, is greater than the pressure in the pleural space surrounding the alveoli. If, in the expiration phase, the pressurization of the airways is reversed again by the ventilation device, this has the result that the lung tissue relaxes and the airway pressure or alveolar pressure drops. In some circumstances, this kind of positive pressure ventilation can have the effect that the pressure conditions in the airways or in the alveoli at the end of the expiration phase are unfavorable and lead to a collapse of some of the alveoli. The collapsed part of the lung volume then has to be opened up again in the subsequent respiratory cycle. The functional residual capacity of the lungs is adversely affected by this, such that the oxygen saturation in the blood of the patient decreases and the lung tissue may also become damaged.

A result of every lung collapse is that, between the closed and the open lung regions, there is an unstable zone in which the fragile alveoli cyclically change state during a breath. They open with each inspiration and collapse as soon as the pressure within them reduces again during expiration. This damages the lungs. This mechanism of damage is referred to as "cyclic recruitment" or also "tidal recruitment", which leads to what is called "biotrauma", namely a local, and later systemic, inflammatory reaction. Simple recruitment is in turn to be understood as the simple opening of possibly collapsed parts or alveoli of the lungs.

To prevent a collapse of alveoli at the end of the expiration phase, a positive end-expiratory pressure (PEEP) is generally set in positive-pressure machine ventilation.

In artificial ventilation with a positive end-expiratory pressure (PEEP), the ventilator applies a predetermined positive pressure, the positive end-expiratory pressure (PEEP), to the airways. The positive end-expiratory pressure (PEEP) is therefore still present at the end of the expiration phase.

It is important here to set the positive end-expiratory pressure (PEEP) if possible in such a way that, during the expiration phase, the alveolar pressure does not fall below the pressure in the pleural space or at any rate falls only so far that the alveolar tissue does not collapse under the effect of the pressure in the pleural space. However, if the positive end-expiratory pressure (PEEP) that has been set has too high a value, this can also have negative consequences, particularly during the inspiration phase. This is because the tidal volume that has to be applied in the inspiration builds on the PEEP (residual pressure in the lungs), such that, through the additionally applied lung volume, the lung tissue can lead to very high airway pressures, and this may lead to an end-inspiratory overdistension. This results in excessive local stress on the lungs.

It must be borne in mind that the lung tissue is damaged both by too low a pressure at the end of exhalation and also by too high a pressure at the end of inhalation. If the pressures remain too high or too low throughout the respiratory cycle and over a long period of time (many minutes, hours, days or weeks), this can negatively impact the cardiovascular system and also the thin-walled tissue structure of the lungs. These mechanical and biochemical effects can lead to a wide variety of complications. The spectrum extends from the release of stress hormones during breathing to the reduction of the functional lung regions and the tearing of lung tissue.

Before carrying out any prolonged ventilation therapy, it is therefore important to systematically explore the scope between overdistension and collapse.

WO 2005/092415 A1, the entire disclosure of which is incorporated by reference herein, has already disclosed an approach to observing the state of the lungs in a non-invasive manner, from which it is possible to draw conclusions regarding the desired gas exchange in the lungs.

The present invention proceeds from WO 2005/092415 A1.

In WO 2005/092415 A1, an attempt is initially made, in a first step, to open collapsed parts of the lungs by means of a targeted increase in the airway pressures, which is designated as "recruitment". These high pressures have the effect merely of achieving a brief distension of the lungs, in order if possible to bring the whole lung tissue to the "open" state. Proceeding from this, the initially high opening pressures are lowered quickly and strikingly to a safe level in a second step, and they are then further reduced, in a third step called "PEEP titration", over quite a long period of time in small steps.

During this entire process, the lung mechanics and carbon dioxide concentration ($CO_2$ concentration) of the exhaled air are measured and observed as patient-specific physiological parameters. The PEEP titration equates to a technical identification routine and serves to determine the "work point", i.e. the pressure level at which the subsequent ventilation therapy can safely take place over a long period of time.

For the artificial ventilation of patients, it is therefore desirable to be able to observe the pulmonary stress as closely as possible in order to draw conclusions regarding any excessively high end-inspiratory pressures or excessively low end-expiratory pressures (PEEP) or to draw conclusions quite generally concerning other parameters that characterize the artificial ventilation. In this sense, during the operation of a ventilator for artificial ventilation of a patient, patient-specific physiological parameters are recorded, on the one hand, and technical respiration parameters are set on the ventilator, on the other hand, on the basis of which parameters the patient is ventilated.

In view of the foregoing, it would be advantageous to have available a method for operating a ventilator for artificial ventilation of a patient, by means of which method the artificial ventilation process can be safely controlled, on the one hand without the patient being undersupplied, and, on the other hand, without too great a strain being placed on the patient's lungs by the artificial ventilation.

It further would be advantageous to have available a ventilator for artificial ventilation of a patient, which ventilator automatically controls the artificial ventilation of the lungs in a reliable manner, such that, on the one hand, the patient is not undersupplied, and, on the other hand, the patient's lungs are not subjected to too great a strain by the artificial ventilation.

SUMMARY OF THE INVENTION

The invention provides among other things a method for operating a ventilator for artificial ventilation of a patient as set forth in the independent claims.

The dependent claims relate to various advantageous developments of the present invention which are independent of one another and of which the features can, within the scope of what is technically meaningful, be freely combined with one another by a person of skill in the art. In particular, this also applies beyond the boundaries of the various claim categories.

In detail, according to a first aspect of the invention, a method is proposed for operating a ventilator for artificial ventilation of a patient, wherein the following steps take place: initial recording of at least one patient-specific physiological parameter, initial setting of at least one technical respiration parameter, and ventilation of the patient on the basis of the technical respiration parameter. The method is characterized in that the at least one technical respiration parameter corresponds to at least one of the respiration parameters comprising respiratory minute volume, tidal volume, respiratory rate, positive end-expiratory pressure, or the inspiratory oxygen concentration made available by the ventilator.

Moreover, according to the proposed method, a repeating measurement of the at least one patient-specific physiological parameter is carried out by the ventilator at time intervals. Finally, an adaptation of the at least one technical respiratory parameter is effected by the ventilator on the basis of the repeating measurement of the patient-specific physiological parameter.

Essential to the present invention is the recognition that the functional state of the ventilated lungs changes from one breath to the next breath of the artificially ventilated patient and is incorporated in the regulation of the respiration settings. By the simultaneous incorporation both of technical and also of physiological variables, on the one hand in the form of technical respiration parameters and on the other hand in the form of patient-specific physiological parameters, into the regulation of the ventilator, a new dimension in ventilation therapy is achieved. This approach permits safe control of the ventilation therapy, even under the difficult circumstances faced today in modern intensive care medicine, namely with patients being kept in place for shorter periods despite having increasingly more serious diseases.

By means of the proposed method, the corresponding ventilator can observe the state of the lungs in an automated manner via the patent-specific physiological parameters and, at regular intervals, can automatically adapt the technical respiration parameters in such a way as to ensure successful and gentle artificial ventilation of the patient.

According to a first advantageous embodiment of the method, the at least one patient-specific physiological parameter can correspond to at least one of the parameters comprising airway dead space, alveolar dead space, or physiological dead space of the patient.

According to a first advantageous embodiment of the method, the repeating measurement of the at least one patient-specific physiological parameter can be carried out after each breath by the patient. In this way, a type of real-time control of safe artificial ventilation can be carried out in a particularly advantageous manner. The artificial ventilation can be adapted directly via the technical respiration parameters to be set as soon as the analysis after one breath shows that the functional state of the lungs, or the result of the artificial ventilation, is not the desired state or result.

It is thus particularly advantageous that the functional state of the lungs is determined anew against the background of the respective respiration setting for each breath, and the decision is taken as to whether the lungs are already being optimally ventilated or whether the ventilation requires further optimization.

Further preferably, the repeating measurement of the at least one patient-specific physiological parameter can be effected by means of capnography, preferably volumetric capnography, by the ventilator, and the at least one patient-specific physiological parameter can correspond to at least one parameter directly representing the $CO_2$ gas exchange in the lungs of the patient, preferably at least one of the parameters comprising end-expiratory $CO_2$ partial pressure in the exhaled gas mixture, alveolar $CO_2$ partial pressure, or the volume of $CO_2$ eliminated by the patient in a single breath.

Capnography is a suitable means for determining and graphically representing the amount or proportion of the expiratory carbon dioxide, or expiratory $CO_2$. The $CO_2$ kinetics of machine-ventilated patients are presented non-invasively and in real time. Volumetric capnography in particular represents a suitable means for the clinical monitoring of machine-ventilated patients.

By means of capnography, the $CO_2$ concentration in respiratory gases can be measured during the respiratory cycle. The $CO_2$ concentration is generally calculated by the absorption of infrared light according to the Beer-Lambert law and is usually expressed as partial pressure in mmHg. The graphical presentation of the $CO_2$ elimination during respiration is referred to as a capnogram, and the corresponding measuring device as a capnograph.

So-called sidestream capnographs are devices which aspirate a respiratory gas sample from the airway opening of the ventilated patient, transport it via a hose system to measuring devices located remote from the aspiration site, in order there to measure the $CO_2$ contained in the sample. They cope better with humid respiratory gases and do not cause any additional instrumental dead space. By contrast, mainstream capnographs are devices in which the $CO_2$ sensors and in many cases also the flow sensors are located in a measurement head on the Y-piece of the breathing hose of the ventilator, such that, with this method, in situ measurements can be carried out near the airway opening. Mainstream capnographs do not cause any volume losses and they measure the whole respiratory gas volume. Both sidestream capnographs and mainstream capnographs can be used within the context of the present invention; the capnographs mentioned preferably and advantageously constitute an integral part of the corresponding ventilator.

Capnography is generally classified according to its graphical representation, wherein time-based or standard capnography is the most widely used capnogram. Here, the $CO_2$ concentration is plotted over time. By contrast, volume-based capnography or volumetric capnography represents the amount of the carbon dioxide eliminated in one breath via the exhaled volume of the breath. In contrast to standard capnography, volumetric capnography can advantageously record volumetric parameters that are of clinical importance. These include the pulmonary elimination of $CO_2$, the dead space and the alveolar aeration. Both time-based or standard capnography and also volume-based or volumetric capnography can be used in the context of the present invention, wherein the two methods of presenting and evaluating the elimination of $CO_2$ can also be used in combination in the proposed method and in the corresponding ventilator.

The patient-specific physiological parameter of the amount of $CO_2$, or specifically the volume of $CO_2$, eliminated in a single breath by the patient can be determined non-invasively by volumetric capnography by means of integration of the expiratory $CO_2$ over the expiratory tidal volume.

In the course of the proposed method, the diffusion of the $CO_2$ can thus be used as the patient-specific physiological parameter representing the success of the artificial ventilation, in order to automatically draw conclusions for adapting the at least one technical respiration parameter. It is thus possible to ensure an artificial ventilation that is physiologically successful but also gentle on the patient.

According to a further advantageous embodiment of the proposed method, the repeating measurement of the at least one patient-specific physiological parameter can be effected by means of oxygraphy, preferably volumetric oxygraphy, by the ventilator, and the at least one patient-specific physiological parameter corresponds to at least one of the parameters comprising alveolar $O_2$ partial pressure and/or the volume of the oxygen taken up by the patient in one breath. Analogously to the above-discussed parameter directly representing the $CO_2$ gas exchange in the patient's lungs, as the patient-specific physiological parameter, it is alternatively or additionally possible to advantageously use, as the patient-specific physiological parameter, the parameter directly representing the oxygen gas exchange ($O_2$ gas exchange) in the patient's lungs.

According to a further advantageous embodiment of the proposed method, the at least one patient-specific physiological parameter can correspond to at least the parameter arterial $CO_2$ partial pressure, wherein the arterial $CO_2$ partial pressure is approximated via non-invasively measured patient-specific physiological parameters.

The values of the arterial $CO_2$ partial pressure ($PaCO_2$) or else also of the arterial $O_2$ partial pressure ($PaO_2$) are the products of the gas exchange in the lungs and can thus be used to assess the efficiency of the gas exchange. However, the determination thereof is traditionally done invasively by means of arterial blood gas analysis (BGA). The normal PaCO2 value is 40±3 mmHg, and deviations from this value define either hypercapnia ($PaCO_2$>45 mmHg) or hypocapnia ($PaCO_2$<35 mmHg).

However, the main disadvantages of blood gas analysis are that it is neither a non-invasive measurement method nor a continuous measurement method. Its results are therefore also only representative of the moment at which the blood was sampled. However, since machine ventilation is a continuous treatment, it would actually be desirable to use non-invasive and especially also continuous monitoring methods in order to assess the gas exchange. Here, pulse oximetry and capnography provide targeted real-time information concerning the biologically most important gases $O_2$ and $CO_2$, and this is in most cases sufficient in largely healthy patients on ventilators. By contrast, in the case of more complex pathologies, blood gas analyses should also be added to these values.

By means of the proposed method, it is also possible to further approximate the arterial $CO_2$ partial pressure ($PaCO_2$) non-invasively, advantageously by means of capnography. For this purpose, it is possible to determine the arterial end-tidal $CO_2$ gradient (Pa-$ETCO_2$) or the arterial alveolar $CO_2$ difference (Pa-$ACO_2$). Then, by means of capnography, the $PaCO_2$ value can be approximated, by means of a difference calculated in this way being added to the non-invasive $PETCO_2$ or $PACO_2$ values. The normal Pa-$ETCO_2$ difference is ≤5 mmHg, and that for Pa-$ACO_2$ is approximately 5 mmHg to 8 mmHg. The Pa-$ACO_2$ difference is the more suitable index since it represents the averaged value of the whole alveolar compartment, whereas $PaCO_2$ does this in relation to the vessels. Pa-$ACO_2$, like the PA-$aO_2$ index derived from oxygen, is suitable for estimating the diffusion at the alveolar-capillary membrane.

According to a further advantageous embodiment of the proposed method, the repeating measurement of the at least one patient-specific physiological parameter can be effected by means of pulse oximetry, and the at least one patient-specific physiological parameter corresponds to at least the parameter arterial oxygen saturation of the blood of the patient.

According to a further advantageous embodiment of the proposed method, as the at least one patient-specific physiological parameter, the parameter volumetric blood flow of the intrapulmonary right-to-left shunt of the patient can be determined from the parameters comprising alveolar oxygen concentration, the amount of oxygen taken up by the patient in one breath and/or the arterial oxygen saturation of the blood of the patient. The value of the intrapulmonary right-to-left shunt corresponds to the shunt circulation from the so-called left heart to the right heart. This "shunted" blood flows from the right half of the heart to the left half of the heart, without taking part in the gas exchange. The amount, or the blood volume or the volumetric blood flow, of this blood not taking part in the gas exchange can likewise advantageously serve to further adapt the technical respiration parameters.

In order to determine the extent of the shunt circulation, the inspiratory oxygen concentration for example can be lowered in stages from high concentrations to the ambient air level, and the resulting corresponding oxygen saturation values ($SpO_2$ values) can be determined. The pairs of values are then joined to one another to form a curve, and their profile is compared with the so-called iso-shunt curves determined beforehand on the basis of physiological relationships, after which the relevant shunt value is read off. In a development of the proposed method, more physiologically pertinent shunt values can be obtained if, in these calculations, the inspiratory oxygen concentration ($FiO_2$) is replaced by the actually measured alveolar oxygen partial pressure ($PAO_2$), which is determined as described above.

According to a further advantageous embodiment of the proposed method, a recruiting maneuver can be carried out at the start of the artificial ventilation, wherein lung overdistension is achieved by initial provision of an increased ventilation pressure, and then the ventilation pressure is reduced and a PEEP titration is carried out. In this way, a sequence control with $CO_2$-assisted regulation can be integrated in the ventilator. The recruitment maneuver along with PEEP titration serves the purpose of ensuring that as much lung tissue as is reasonably possible is made available both for the breath-by-breath mechanical ventilation and also for the gas exchange. By virtue of this systematic approach, states of lung overdistension and also of lung collapse are identified and can then be avoided by deliberate adaptation to the respiration settings.

According to a further advantageous embodiment of the proposed method, the ventilation pressure amplitude can be permanently monitored during the artificial ventilation, wherein an alarm is triggered if a preset maximum ventilation pressure amplitude is exceeded. By virtue of such monitoring of the ventilation pressure amplitude with corresponding alarm functions, it is possible for indications of a loss of functional lung volume to be provided at an early stage, and suitable therapy measures can be taken as early on as possible. These measures not only include ones that can be carried out directly by means of the ventilator, but also ones that require the intervention of the clinical personnel. These measures can comprise: more far-reaching diagnostic measures (e.g. pulmonary ultrasound, CT scans), targeted positioning of patients, drainage of free air or liquids, etc.

According to a further aspect of the teaching, a ventilator for artificial ventilation of a patient is proposed. The proposed ventilator comprises: a measuring device, which is configured to record at least one patient-specific physiological parameter; a control device, which is configured to set at least one technical respiration parameter, wherein the ventilation of the patient takes place on the basis of the technical respiration parameter, wherein the at least one technical respiration parameter corresponds to at least one of the respiration parameters comprising respiratory minute volume, tidal volume, respiratory rate, positive end-expiratory pressure, or the inspiratory oxygen concentration made available by the ventilator; and a regulator unit, which is in communication with the measuring device and with the control device. The measuring device is configured in such a way that it carries out a repeating measurement of the at least one patient-specific physiological parameter at time intervals. The regulator unit is configured in such a way that it carries out an adaptation of the at least one technical respiration parameter on the basis of the repeating measurement of the patient-specific physiological parameter.

The proposed ventilator for artificial ventilation of a patient is preferably configured to be operated by means of an above-described method, according to one of the instant claims, for operating a ventilator.

The specific effects and advantages of this method have already been described above in respect of the method for operating a ventilator. Reference is here made to these.

Particularly essential as regards the ventilator is the recognition that the functional state of the ventilated lungs changes from one breath to the next breath of the artificially ventilated patient and is incorporated in the regulation of the respiration settings. By the simultaneous incorporation both of technical and also of physiological variables, on the one hand in the form of technical respiration parameters and on the other hand in the form of patient-specific physiological parameters, into the regulation of the ventilator, a new dimension in ventilation therapy is achieved. This approach permits safe control of the ventilation therapy, even under the difficult circumstances faced today in modern intensive care medicine, namely with patients being kept in place for shorter periods of time, despite having increasingly serious diseases.

The proposed ventilator can observe the state of the lungs in an automated manner via the patient-specific physiological parameters and, at regular intervals, can automatically adapt the technical respiration parameters in such a way as to ensure successful and gentle artificial ventilation of the patient.

According to a first advantageous embodiment of the ventilator, provision is made that the at least one patient-specific physiological parameter corresponds to at least one of the parameters comprising airway dead space, alveolar dead space, or physiological dead space of the patient.

According to a further advantageous embodiment of the ventilator, provision is made that the measuring device is moreover configured in such a way that it carries out the repeating measurement of the at least one patient-specific physiological parameter after each breath taken by the patient.

According to a further advantageous embodiment of the ventilator, provision is made that the measuring device is designed as a capnograph and is configured in such a way that it carries out the repeating measurement of the at least one patient-specific physiological parameter by means of capnography, preferably volumetric capnography, and that the at least one patient-specific physiological parameter corresponds to at least one parameter directly representing the $CO_2$ gas exchange in the lungs of the patient, preferably at least one of the parameters comprising end-expiratory $CO_2$ partial pressure in the exhaled gas mixture, alveolar $CO_2$ partial pressure, or the volume of $CO_2$ eliminated in a single breath by the patient.

According to a further advantageous embodiment of the ventilator, provision is made that the measuring device is configured in such a way that it carries out the repeating measurement of the at least one patient-specific physiological parameter by means of oxygraphy, preferably volumetric oxygraphy, and that the at least one patient-specific physiological parameter corresponds to at least one of the parameters comprising alveolar $O_2$ partial pressure and/or the volume of the oxygen taken up by the patient in one breath.

According to a further advantageous embodiment of the ventilator, provision is made that the at least one patient-specific physiological parameter corresponds to at least the parameter arterial $CO_2$ partial pressure, wherein the measuring device is configured in such a way that it approximates the arterial $CO_2$ partial pressure via non-invasively measured patient-specific physiological parameters.

According to a further advantageous embodiment of the ventilator, provision is made that the measuring device is designed as a pulse oximeter and is configured in such a way that it carries out the repeating measurement of the at least one patient-specific physiological parameter by means of pulse oximetry, and that the at least one patient-specific physiological parameter corresponds at least to the parameter arterial oxygen saturation of the blood of the patient.

According to a further advantageous embodiment of the ventilator, provision is made that the measuring device is configured in such a way that, as the at least one patient-specific physiological parameter, it determines the parameter volumetric blood flow of the intrapulmonary right-to-left shunt of the patient from the parameters comprising alveolar oxygen concentration, the amount of oxygen taken up by the patient in one breath and/or the arterial oxygen saturation of the blood of the patient.

According to a further advantageous embodiment of the ventilator, provision is made that the control device is configured in such a way that it carries out a recruiting maneuver at the start of the artificial ventilation, wherein lung overdistension is achieved by initial provision of an increased ventilation pressure, and then the ventilation pressure is reduced and a PEEP titration is carried out.

According to a further advantageous embodiment of the ventilator, provision is made that a monitoring unit is provided, which is configured in such a way that the ventilation pressure amplitude is permanently monitored during the artificial ventilation, wherein an alarm is triggered if a preset maximum ventilation pressure amplitude is exceeded.

The advantages of the proposed ventilator or of its preferred embodiments are clear from the above-described proposed method for operating a ventilator, and therefore reference is made in this respect to the description of the method.

BRIEF DESCRIPTION OF THE DRAWINGS

Preferred embodiments of the invention are described by way of example with reference to the accompanying figures, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
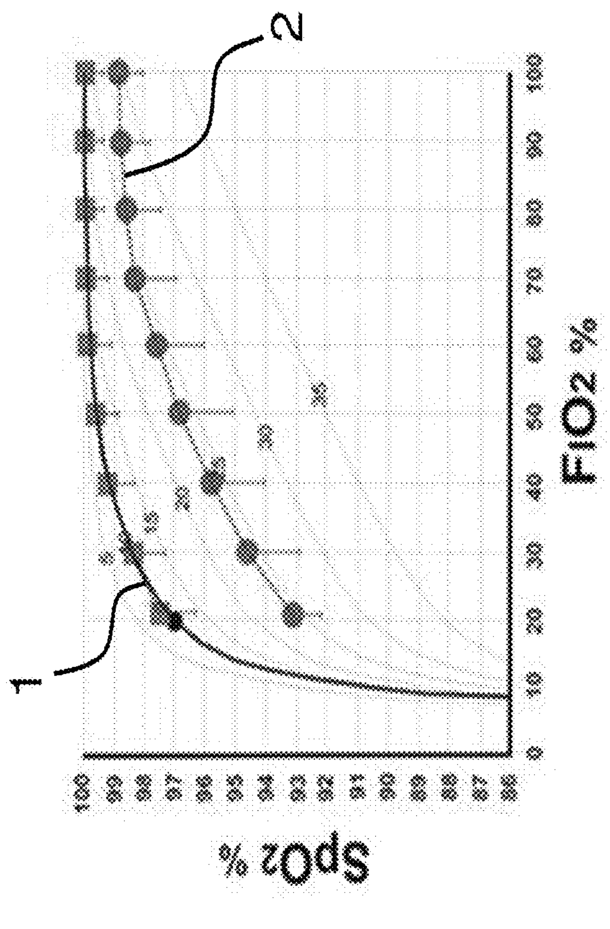
FIG. 1 shows an exemplary diagram on the basis of which the right-to-left shunt in a patient can be determined.

Two examples of curves 1, 2 are shown in FIG. 1, wherein the value pairs have been labeled with squares on curve 1 and with circles on curve 2. Measured oxygen saturation values ($SpO_2$ values) of an artificially ventilated patient are plotted on the y axis for different inspiratory oxygen concentrations ($FiO_2$) that have been made available by the ventilator, which are plotted on the x axis.

In order to determine the right-to-left shunt in the lungs, the inspiratory oxygen concentration $FiO_2$ is lowered in stages from high concentrations to the ambient air level, and the resulting corresponding $SpO_2$ values are determined via the measuring device of the proposed ventilator. These points are then connected to one another to form a curve 1 or 2, and their profile is compared with the iso-shunt curve determined beforehand on the basis of physiological relationships, and then the matching shunt value is read off.

These iso-shunt curves are plotted as fine lines with associated shunt values in FIG. 1 in the diagram. The approximated shunt values can be read off from the correspondence of the measured curves with the iso-shunt curves. Here, curve 1 corresponds to a right-to-left shunt of ca. 24%, while curve 2 corresponds to a right-to-left shunt of less than 10%.

Figure 2:
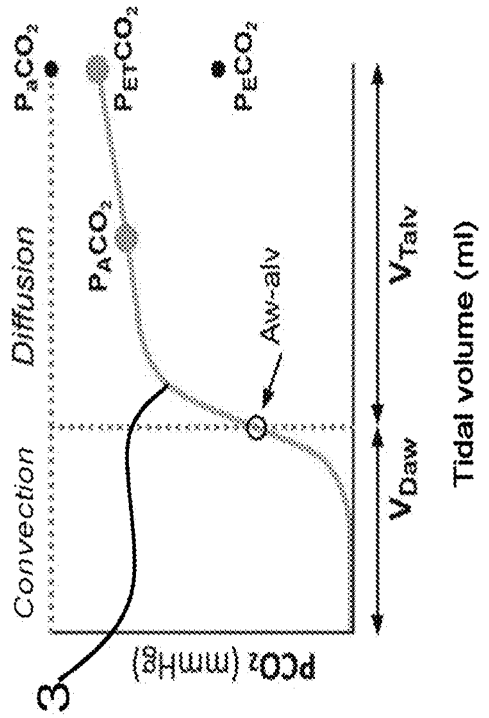
FIG. 2 shows a typical diagram of volumetric capnography, and the most important values that can be derived therefrom for the artificial ventilation.

FIG. 2 shows a diagram of volume-based capnography and of the most important parameters thereof. Such a diagram can be integrated in the proposed ventilator and, in addition, the medical personnel providing the treatment can be shown this diagram on a display unit, for example a display screen.

In the diagram, the measured $CO_2$ partial pressure $PCO_2$ of the exhaled air is plotted in mmHg on the y axis, and the tidal volume $V_T$ is plotted in ml on the x axis. Various patient-specific physiological parameters important for ventilation can be read off from the indicated curve 3.

Examples of these are the following clinically important $CO_2$ partial pressures: $PETCO_2$ as end-tidal $CO_2$ partial pressure, $PACO_2$ as mean alveolar CO2 partial pressure, and $P\bar{E}CO_2$ as the mixed expiratory CO2 partial pressure. The mixed expiratory $CO_2$ partial pressure $P\bar{E}CO_2$ derives from the dilution effect that arises as a result of the physiological dead space $V_{Dphys}$. These are all patient-specific physiological parameters that can generally be measured by the measuring device of the ventilator and can then serve as a basis for the adaptation of the technical respiration parameters.

Further patient-specific physiological parameters are $PaCO_2$ as the $CO_2$ partial pressure in the arterial blood, which is analyzed by means of blood sampling and appears as a dotted line at the top in the capnogram. The mathematical reversal point of the capnogram—the interface between airways and alveoli—is the boundary between the airway dead space $V_{Daw}$ and the alveolar tidal volume $V_{Talv}$.

The dead space volume is generally attributable to the fact that, in each respiratory cycle, a proportion of the tidal volume $V_T$ remains in the air-conducting airways and does not therefore reach the alveolar compartment. This proportion is called airway dead space $V_{Daw}$. In artificially ventilated patients, there is often an additional instrumental dead space $V_{Dinst}$, which is caused by components of the ventilator, such as connectors, angle pieces or humidifying filters or microbe filters, which are placed between the Y-piece and the endotracheal tube in the ventilator. In addition to all this, there is also what is known as the alveolar dead space $V_{Dalv}$. This results from alveoli which, although supplied with air, are not perfused. Accordingly, these alveoli also do not take part in the gas exchange. The airway dead space $V_{Daw}$ and the alveolar dead space $V_{Dalv}$ together determine the total dead space $V_D$, which is also referred to as the physiological dead space $V_{Dphys}$.

The total dead space $V_D$ can be determined by means of volumetric capnography. For this purpose, use is made of the Fowler concept, which is based on the Bohr formula. Fowler postulated that the boundary between the convective gas transport in the air-conducting airways (dead space) and the diffusive gas transport is formed by the interface between airways and alveoli, which interface is in turn represented by the reversal point of the $CO_2$ profile in the capnogram, cf. FIG. 2. This approach allows the airway dead space $V_{Daw}$ of each breath to be determined repetitively and non-invasively.

The Bohr formula is a mass balance equation in which the proportion of the tidal volume $V_T$ that does not contain $CO_2$ is calculated as follows:

$V_{Dphys}/V_T = V_D/V_T = (PACO_2 - P\bar{E}CO_2)/(PACO_2 - PICO_2)$ where $PICO_2$ is the inspired $CO_2$ partial pressure at which, under normal circumstances, a value of zero is assumed, since the fresh gas ought not to contain $CO_2$. However, for adequate calculation of the dead space, this value always has to be taken into account, because some of the $CO_2$ rebreathing stems from the Y-piece of the ventilator and from an additional instrumental dead space $V_{Dinst}$. Finally, the alveolar dead space $V_{Dalv}$ is calculated by subtracting the airway dead space $V_{Daw}$ from the physiological dead space $V_{Dphys}$.

The dead space $V_D$ or $V_{Dphys}$ can be expressed as part of the minute ventilation in l/min or as an absolute value of one breath, as physiological dead space $V_{Dphys}$ in ml, or else as a ratio to the tidal volume $V_D/V_T$. The latter ratio is most suitable, since the dead space $V_D$ or $V_{Dphys}$ is greatly influenced by the extent of the tidal volume $V_T$. The dead space ratios, standardized to the expired volume, permit comparison between persons of different weight, who are ventilated with different tidal volumes $V_T$.

For the clinical applications, it is important to know the physiological dead space values $V_{Dphys}$. In healthy and young, spontaneously breathing patients, the ratio of physiological dead space $V_{Dphys}$ to tidal volume $V_T$ ($V_{Dphys}/V_T$) is approximately 20-25%, divided into the ratios airway dead space $V_{Daw}$ to tidal volume $V_T$($V_{Daw}/V_T$) with ca. 15-20% and alveolar dead space $V_{Dalv}$ to tidal volume $V_T$ ($V_{Dalv}/V_T$) with about 5-9%.

In patients with healthy lungs, machine ventilation increases the ratio physiological dead space $V_{Dphys}$ to tidal volume $V_T$ ($V_{Dphys}/V_T$) to 30-40%, while this value in intensive-care patients is over 40%. In patients with chronic pulmonary diseases, there are increased physiological dead spaces $V_{Dphys}$ of more than 50%, whereas the airway dead space $V_{Daw}$ and the alveolar dead space $V_{Dalv}$ may be increased by two to three times compared to the normal value.

In an article by Enghoff (*Enghoff H. Volum inefficax. Bemerkungen zur Frage des schädlichen Raumes. Upsala Läk Fören Förch* 1938; 44: 191-218), the Bohr formula was modified by replacing the alveolar $CO_2$ partial pressure $PACO_2$ with the arterial $CO_2$ partial pressure $PaCO_2$, because the alveolar $CO_2$ partial pressure $PACO_2$ was not measurable at the bedside. However, this invasive and intermittent calculation method, using blood gas analysis, systematically overestimates the dead space $V_D$, because the value of the arterial $CO_2$ partial pressure $PaCO_2$ is normally always higher than the alveolar $CO_2$ partial pressure $PACO_2$ influenced by the dead space $V_D$ and the shunt effect. However, with the method proposed according to the invention, the Bohr formula can in practice be used completely non-invasively, since the determination of the alveolar $CO_2$ partial pressure $PACO_2$ and the mixed-expiratory $CO_2$ partial pressure $P\bar{E}CO_2$ is technically possible from the volumetric capnogram and is integrated in the ventilator proposed according to the invention.

With the volumetric capnography tool presented here, the dead space proportion of the tidal volume and thus the efficiency of the ventilation can be determined at the bedside, wherein an additional arterial blood gas analysis can also deliver an additional and reliable estimate of the shunt.

On the basis of its voltage-based values, the capnography delivers information on the $CO_2$ diffusion in an entirely non-invasive manner. The end-expiratory $CO_2$ partial pressure in the exhaled gas mixture $PETCO_2$ is the best known parameter of capnography. It represents the $CO_2$ partial pressure in peripheral lung portions, or in those with a long time constant, where emptying into the large airways takes place after a delay. By contrast, the alveolar $CO_2$ partial pressure $PACO_2$ represents all lung units with different time constants. For many years it was assumed that this value could not be measured at the bedside. With the method proposed according to the invention, the alveolar $CO_2$ partial pressure $PACO_2$ can be determined precisely as the midpoint of the rise from the last phase of the capnogram curve shown in FIG. 2. The reason for this is that such a point has to represent the averaged $CO_2$ value in all alveoli, since this last phase is determined only by the gases in the alveoli. In this way, by means of the method proposed according to the invention, alveolar ventilation and dead spaces can advantageously be determined breath by breath and non-invasively.

The alveolar $CO_2$ partial pressure $PACO_2$ can now likewise be used, in addition to the end-expiratory $CO_2$ partial pressure in the exhaled gas mixture $PETCO_2$, for the approximation of the arterial $CO_2$ partial pressure $PaCO_2$. However, it must always be clear that, ultimately, the clinically important arterial $CO_2$ partial pressure $PaCO_2$ cannot be replaced either by the end-expiratory $CO_2$ partial pressure in the exhaled gas mixture $PETCO_2$ or by the alveolar $CO_2$ partial pressure $PACO_2$: the reason being shunt and dead space effects. Both of these cause the arterial $CO_2$ partial pressure $PaCO_2$ to be usually higher than the alveolar $CO_2$ partial pressure $PACO_2$ and end-expiratory $CO_2$ partial pressure in the exhaled gas mixture $PETCO_2$. On account of the presence of an anatomical shunt and dead space, this even applies to young persons with healthy lungs. Therefore, in critical situations, particularly when important changes to the $CO_2$ kinetics are observed or suspected, a complementary blood gas analysis should be carried out.

However, according to the proposed method, the arterial $CO_2$ partial pressure $PaCO_2$ can be further approximated by means of capnography. This can be achieved by determining the arterial to end-tidal $CO_2$ gradient $Pa\text{-}ETCO_2$ or else the arterial to alveolar $CO_2$ difference $Pa\text{-}ACO_2$. By means of capnography, it is possible to approximate the arterial $CO_2$ partial pressure $PaCO_2$ when a difference calculated in this way is added to the non-invasive values end-expiratory $CO_2$ partial pressure in the exhaled gas mixture $PETCO_2$ or alveolar $CO_2$ partial pressure $PACO_2$.

The normal difference value for the arterial to end-tidal $CO_2$ gradient $Pa\text{-}ETCO_2$ is ≤5 mmHg, and the normal value for the arterial to alveolar $CO_2$ difference $Pa\text{-}ACO_2$ is ~5-8 mmHg. Here, the arterial to alveolar $CO_2$ difference $Pa\text{-}ACO_2$ is the more suitable index, since it represents the averaged value of the whole alveolar compartment, while the arterial $CO_2$ partial pressure $PaCO_2$ does this with reference to the vessels. The arterial to alveolar $CO_2$ difference $Pa\text{-}ACO_2$ is therefore suitable for estimating the diffusion at the alveolar-capillary membrane.

Figure 3:
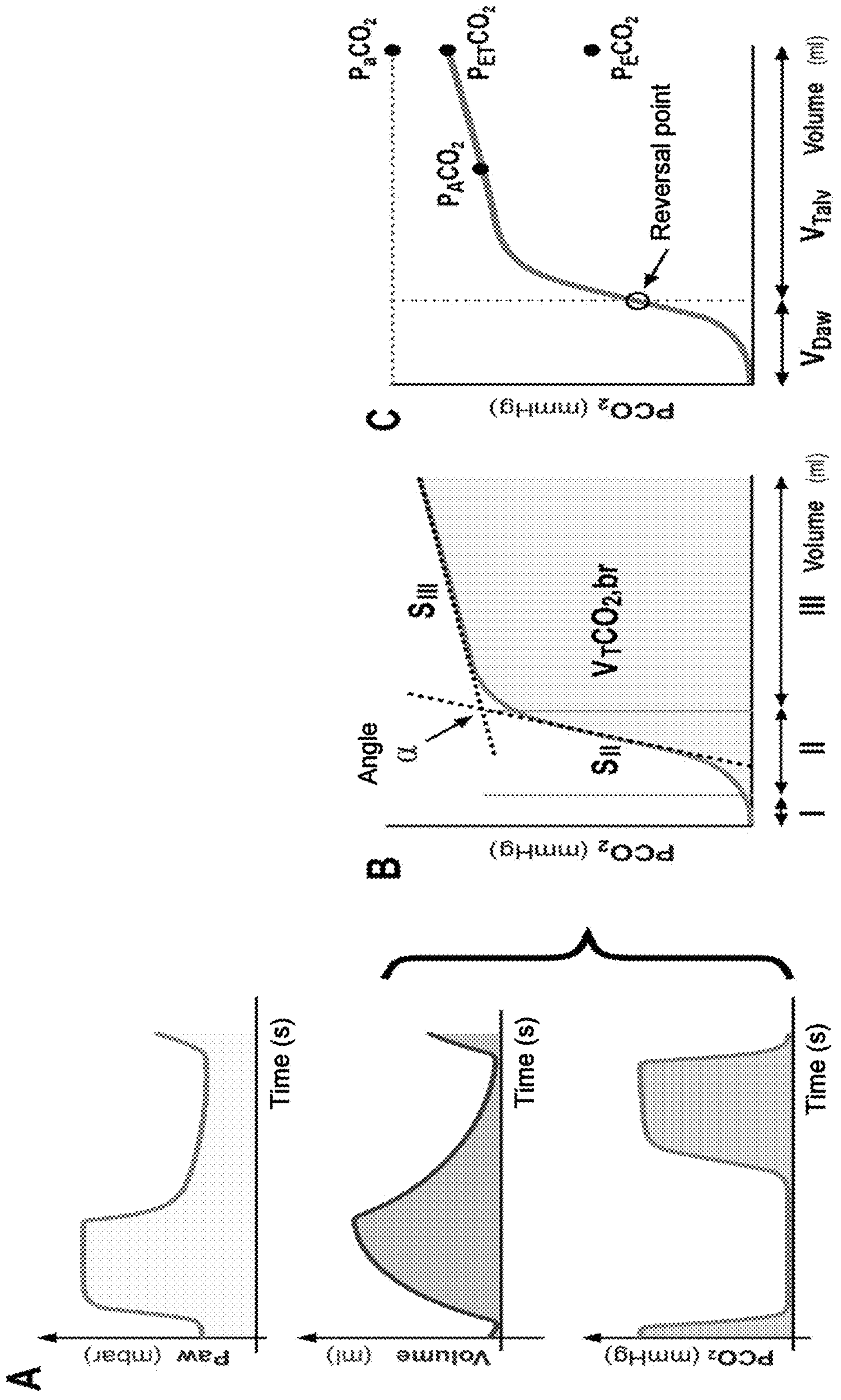
FIG. 3 shows two diagrams representing time-based capnography (left) and volume-based capnography (right).

FIG. 3 shows time-based capnography on the left-hand side and volume-based capnography on the right-hand side. Analogously to the standard capnogram, the volumetric capnogram on the right can be divided into the following three phases: phase I represents the first part of the expiration in which there is no $CO_2$. In this ventilation phase I, approximately 10-12% of the tidal volume $V_T$ is made available. Phase II shows a rapid rise in $CO_2$ during the expiration. In this ventilation phase II, approximately the next 15-18% of the tidal volume $V_T$ are made available. Finally, phase III is reached, in which the proportion of the tidal volume $V_T$ determined only by the gases coming from the alveoli makes up the remaining 70-75% of the tidal volume $V_T$.

The volumetric capnography or the capnogram can be characterized more closely by the gradient of two intersecting straight lines. One straight line is the gradient of phase II and is characterized by the characteristic value $S_{II}$. The normal value of $S_{II}$ is 0.36-0.40 mmHg/ml and is determined by the different $CO_2$ emptying rates from different lung units into the large airways. The other straight line is the gradient of phase III and is characterized by the characteristic value $S_{III}$. The normal value of $S_{III}$ is 0.007-0.017 mmHg/ml, wherein $S_{III}$ is determined mainly by the distribution of aeration and perfusion in the lungs. The angle alpha is the angle formed at the intersection of the straight lines $S_{II}$ and $S_{III}$, wherein the normal value for the angle alpha is 150-1600.

The area under the curve is the most important parameter. The area represents the amount of $CO_2$ that is eliminated in one breath and is labeled with the sign $VTCO_{2,br}$. This value is dependent especially on patient-specific factors and the extent of the tidal volume $V_T$. A typical value of the tidal volume $V_T$ in an adult is ca. 10-30 ml.

A further differentiation relates to values based on partial pressure; these are important parameters of the expiratory $CO_2$ that are used for the calculation of clinical variables, e.g. the dead space $V_D$. The end-expiratory $CO_2$ partial pressure in the exhaled gas mixture $PETCO_2$ has normal values which, in the example shown here, are ca. 33-37 mmHg. $PACO_2$ is the mean alveolar $CO_2$ partial pressure which, on account of the positive gradient in phase III with values of ca. 30-35 mmHg, is generally lower than the corresponding end-expiratory $CO_2$ partial pressure in the exhaled gas mixture $PETCO_2$. $P\bar{E}CO_2$ is the mixed-expiratory $CO_2$ partial pressure, which results from the dilution effect occasioned by the physiological dead space $V_{Dphys}$, wherein the mixed-expiratory $CO_2$ partial pressure $P\bar{E}CO_2$ assumes values of ca. 18-24 mmHg.

The mathematical reversal point (i.e. the point at which the curvature behavior of the capnogram curve changes) represents the mean value of the stationary interfaces between the convective and the diffusive CO2 transport in the lungs. At the end of the inspiration, it is anatomically located near the respiratory bronchioles. This interface between airways and alveoli determines the transfer between the airways and the alveolar compartments.

With each breath, the capnography based on time and the capnography based on time and volume thus both provide, in a non-invasive manner, complementary bedside information concerning all the important functions of the body that take part in the $CO_2$ kinetics.

With the proposed method and the proposed ventilator, artificial ventilation aids are now made available by means of which the artificial ventilation can proceed safely, in particular with the aid of the measurement methods of capnography. Capnography offers advantageous monitoring for machine-ventilated patients. Time-based capnography describes the expiratory $CO_2$ in its chronological sequence and provides real-time information concerning the puffs administered and also qualitative information concerning the $CO_2$ kinetics of the organism. By contrast, volume-based capnography provides clinically relevant volumetric data on the $CO_2$ kinetics. Both methods of capnography are available at the bedside, are non-invasive and provide complementary, clinically relevant information. Volume-based capnography represents a major advance over todays standard measurement of the mechanism of respiration, because it is capable of providing characteristic values of the gas exchange. Volume-based capnography not only measures the $CO_2$ load to be eliminated by the ventilation, it also describes the efficiency and the hemodynamic effects of each breathing mode and the corresponding respiration settings. Volume-based capnography, integrated in the proposed ventilator, thus opens up a new dimension in the monitoring of ventilation and hemodynamics.

Figure 4:
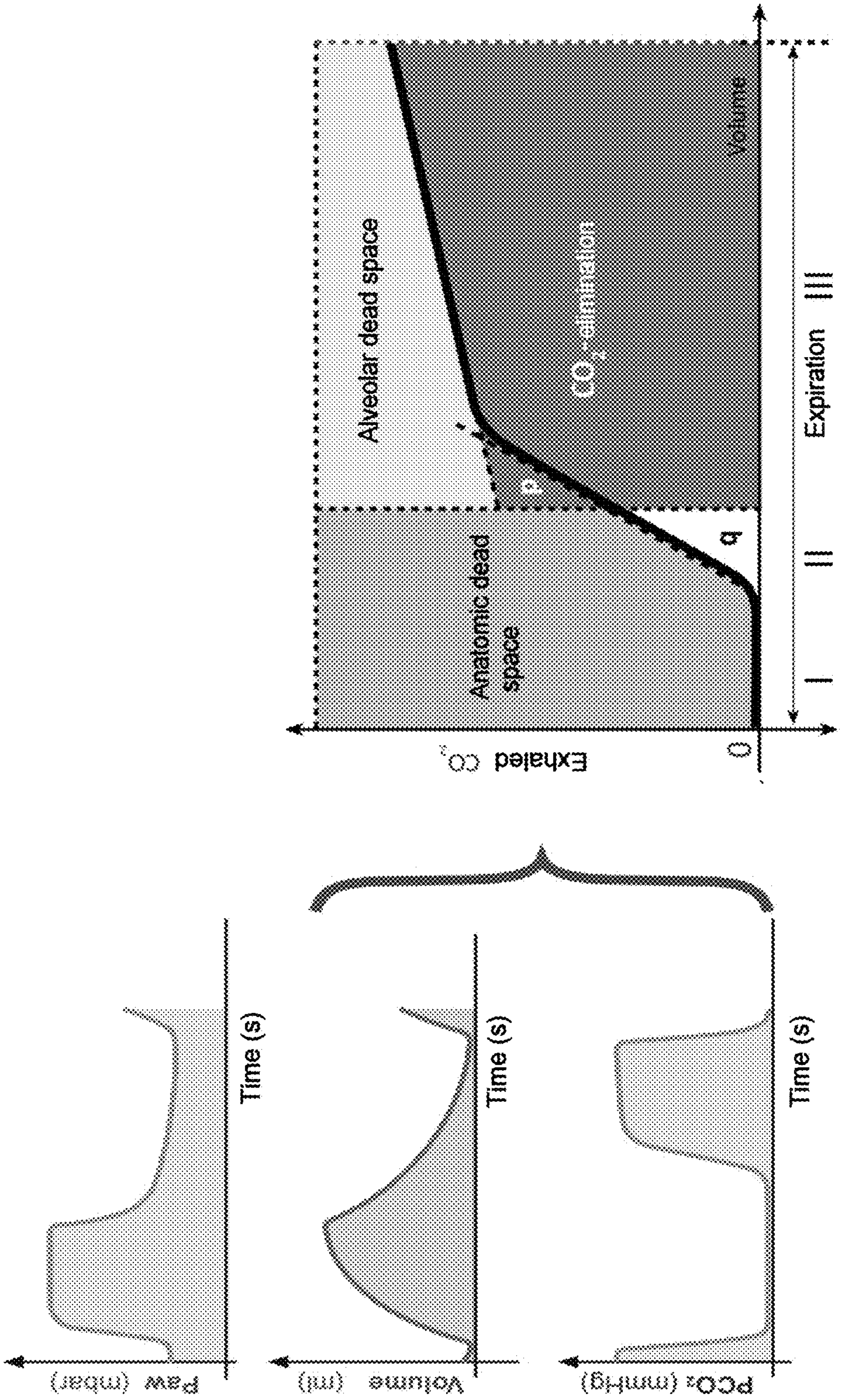
FIG. 4 shows two diagrams representing time-based capnography (left) and volume-based capnography (right), with the dead space proportions.

FIG. 4, analogously to FIG. 3, shows the time-based capnography on the left and the volume-based capnography on the right, with the dead spaces indicated on the right.

Figure 5:
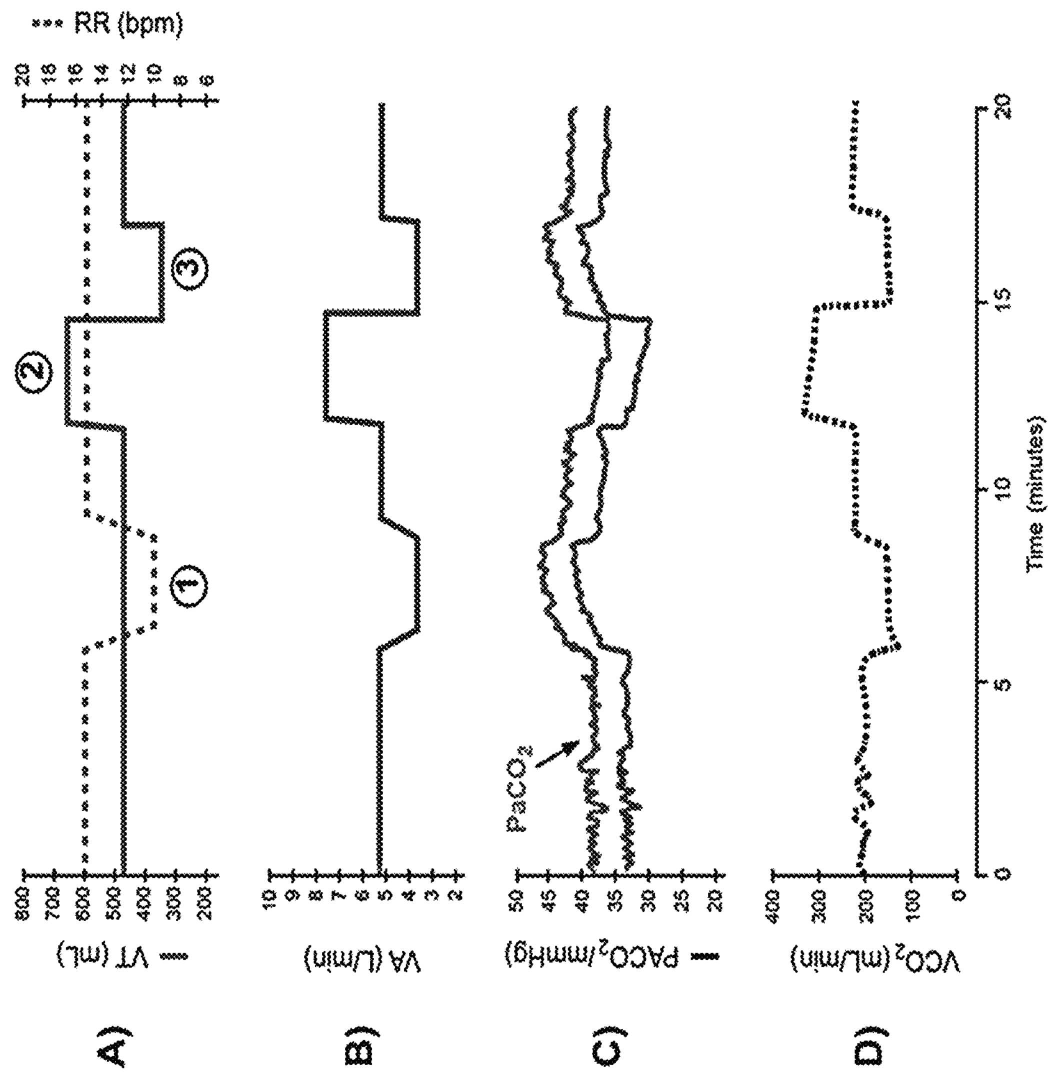
FIG. 5 shows monitoring of the alveolar ventilation on the basis of volumetric capnography.

FIG. 5 shows the profile of different patient-specific physiological parameters in the monitoring of alveolar ventilation on the basis of volumetric capnography. It shows the change of the alveolar ventilation (VA), in the case of a hemodynamically stable patient, by reduction of the respiratory rate (RR) from 15 to 10 breaths per minute (1), by increase (2) and reduction (3) of the tidal volume (VT) during controlled ventilation. The elimination of carbon dioxide ($VCO_2$) and the alveolar $CO_2$ partial pressures ($PACO_2$) behave in opposite senses. The arterial $CO_2$ partial pressure ($PaCO_2$) is shown over the alveolar $PACO_2$ (upper line in C).

Not all parts of the airway—from the mouth and nostrils to the alveoli—actually take part in the gas exchange. In order to assess the effectiveness of the ventilation and, if appropriate, to optimize it, information concerning the proportion of the "effective" alveolar ventilation is very helpful. On account of its high degree of solubility, and therefore its very rapid kinetics, $CO_2$ is an ideal indicator for alveolar ventilation (VA)[2]. Therefore, the measurement and graphic representation of the $CO_2$ partial pressure measured in the exhaled gas mixture ($PETCO_2$) in the form of the capnography curve is recommended for the continuous monitoring of ventilation[1,2]. Examples for the qualitative assessment of the ventilation by means of capnography are: disconnection, apnea, exclusion of incorrect intubation, obstruction, exclusion of patient-ventilator asynchrony, and much more besides. $PETCO_2$ is also used as a quantitative measurement for adjusting the ventilation. In the case of stable hemodynamics and a constant metabolism, a high $PETCO_2$ is an indicator of hypoventilation and a low $PETCO_2$ is an indicator of hyperventilation. Both in practice entail an adaptation of the respiratory minute volume (VE) on the ventilator. Since VE is the product of tidal volume and respiratory rate, it is recommended to modulate these two components for this purpose. In principle, low tidal volumes (VT) are nowadays sought in order, by means of lung-protective ventilation, to avoid volutrauma, biotrauma and barotrauma[3]. What has to be taken into consideration in particular, however, is the fact that, in addition to the alveoli that participate in the gas exchange, dead spaces are also aerated on each breath. The proportion of this dead-space aeration critically influences the efficiency of the ventilation[2,4,52]. For respiratory minute volume, alveolar ventilation (VA) and dead-space ventilation (VD), the following simple formula applies:

$$VE=VA+VD$$

VE is thus composed of an effective part, in which the gas is in contact with the lung capillaries and thus takes part in the gas exchange (alveolar ventilation=VA), and an ineffective part, which does not take part in the gas exchange (dead space=VD)[2]. Thus, VA and its proportion of VE are a measure of the efficiency of respiration and, particularly in someone with limited respiration, VA and VD are important characteristic values for optimization of the ventilation setting.

Accordingly, VA is calculated as:

$$VA=VE-VD$$

Picture 1 shows the importance of VA in the elimination of $CO_2$ in a hemodynamically stable, anesthetized patient. Changes of respiratory rate and VT-induced changes of VA influence the $CO_2$ partial pressures and $CO_2$ elimination ($VCO_2$) in opposite ways. The higher $VCO_2$, with elevated VA, reduces the partial pressures on both sides of the alveolar-capillary membrane, which leads to hypocapnia. Conversely, the lower VA results in a lower $CO_2$ elimination and, consequently, hypercapnia.

Figure 6:
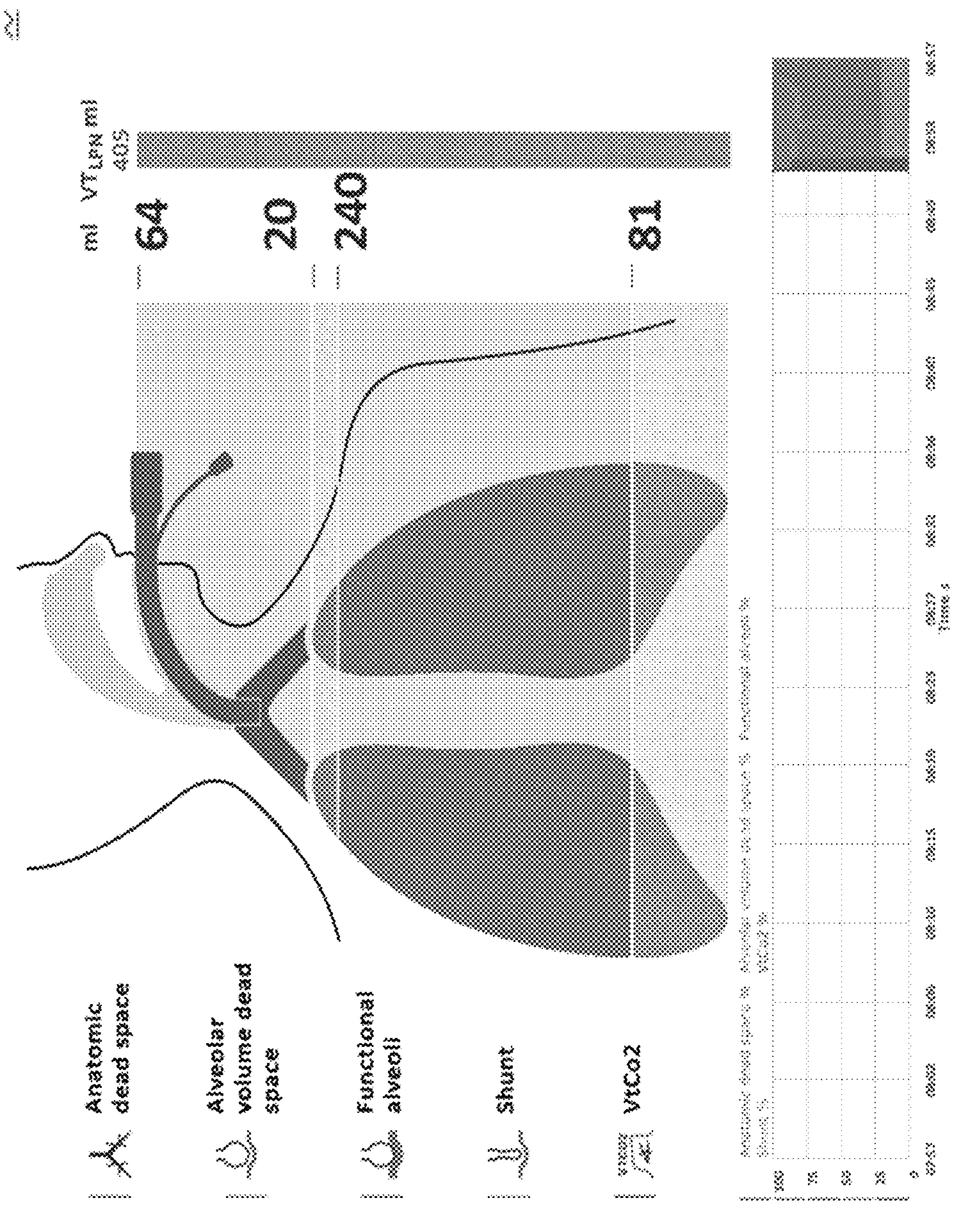
FIG. 6 shows a view on the display of a ventilator.

FIG. 6 shows a view on the display of the ventilator. Based on the recording of at least one patient-specific physiological parameter, proportions (in %) and/or absolute values (in ml) for regions of the lungs/the lung filling were determined here which, relative to at least the one patient-specific physiological parameter, represent anatomic dead space and/or represent alveolar dead space volume and/or represent functional alveoli and/or represent a shunt and/or represent VtCO2. The regions of the lungs are shown differently in a graph, by coloring or hatching, according to their proportions or absolute values and are preferably displayed in a graphic representation of the lungs.

To sum up, the present invention provides:

1. A method for operating a ventilator for artificial ventilation of a patient, which method comprises:
   initial recording of at least one patient-specific physiological parameter,
   initial setting of at least one technical respiration parameter, and
   ventilation of the patient based on the technical respiration parameter,
   wherein the at least one technical respiration parameter corresponds to at least one of the respiration parameters which comprise respiratory minute volume (VE), tidal volume ($V_T$), respiratory rate (RR), positive end-expiratory pressure (PEEP), or an inspiratory oxygen concentration ($FiO_2$) made available by the ventilator,
   wherein a repeating measurement of the at least one patient-specific physiological parameter is carried out by the ventilator at time intervals, and
   wherein an adaptation of the at least one technical respiratory parameter is effected by the ventilator on the basis of the repeating measurement of the patient-specific physiological parameter.
2. The method of item 1, wherein the at least one patient-specific physiological parameter corresponds to at least one of the parameters which comprise airway dead space ($V_{Daw}$), alveolar dead space ($V_{Dalv}$) or physiological dead space ($V_{Dphys}$) of the patient.
3. The method of any one of items 1 or 2, wherein the repeating measurement of the at least one patient-specific physiological parameter is carried out after each breath of the patient.
4. The method of any one of items 1 through 3, wherein the repeating measurement of the at least one patient-specific physiological parameter is effected by means of capnography, preferably volumetric capnography, by the ventilator, and wherein the at least one patient-specific physiological parameter corresponds to at least one parameter directly representing the $CO_2$ gas exchange in the lungs of the patient, preferably at least one of the parameters comprising end-expiratory $CO_2$ partial pressure in the exhaled gas mixture ($PETCO_2$), alveolar $CO_2$ partial pressure ($PACO_2$), or a volume of $CO_2$ eliminated by the patient in a single breath ($VCO_2$).
5. The method of any one of items 1 through 4, wherein the repeating measurement of the at least one patient-specific physiological parameter is effected by means of oxygraphy, preferably volumetric oxygraphy, by the ventilator, and wherein the at least one patient-specific physiological parameter corresponds to at least one of the parameters which comprise alveolar $O_2$ partial pressure ($PCO_2$) and/or volume of oxygen taken up by the patient in one breath ($VO_2$).
6. The method of any one of items 1 through 5, wherein the at least one patient-specific physiological parameter corresponds to at least the parameter arterial $CO_2$ partial pressure ($PaCO_2$), the arterial $CO_2$ partial pressure ($PaCO_2$) being approximated via non-invasively measured patient-specific physiological parameters.
7. The method of any one of items 1 through 6, wherein the repeating measurement of the at least one patient-specific physiological parameter is effected by means of pulse oximetry, and wherein the at least one patient-specific physiological parameter corresponds to at least the parameter arterial oxygen saturation of the blood of the patient ($SpO_2$).
8. The method of any one of items 1 through 7, wherein, as the at least one patient-specific physiological parameter, the parameter volumetric blood flow of the intrapulmonary right-to-left shunt of the patient ($PBF_{SHUNT}$) is determined from the parameters which comprise alveolar oxygen concentration, amount of oxygen taken up by the patient in one breath and/or arterial oxygen saturation of the blood of the patient ($SpO_2$).
9. The method of any one of items 1 through 8, wherein a recruiting maneuver is carried out at the start of an artificial ventilation, wherein lung overdistension is achieved by initial provision of an increased ventilation pressure, and then the ventilation pressure is reduced and a PEEP titration is carried out.
10. The method of any one of items 1 through 9, wherein the ventilation pressure amplitude is permanently monitored during artificial ventilation, an alarm being triggered if a preset maximum ventilation pressure amplitude is exceeded.
11. The method of any one of items 1 through 10, wherein based on a recording of at least one patient-specific physiological parameter, proportions (in %) and/or absolute values (in ml) for regions of the lungs/the lung filling are determined which, relative to at least the one patient-specific physiological parameter, represent anatomic dead space and/or represent alveolar dead space volume and/or represent functional alveoli and/or represent a shunt and/or represent VtCO2, the regions of the lungs being shown differently in a graph (by coloring or hatching) according to their proportions or absolute values and are preferably displayed in a graphic representation of the lungs.
12. A ventilator for artificial ventilation of a patient, preferably configured to be operated by a method according to any one of items 1 through 11, for operating a ventilator, which ventilator comprises:
   a measuring device, which is configured to record at least one patient-specific physiological parameter,
   a control device, which is configured to set at least one technical respiration parameter, wherein the ventilation of the patient takes place on the basis of the technical respiration parameter, at least one technical respiration parameter corresponding to at least one of the respiration parameters which comprise respiratory minute volume (VE), tidal volume ($V_T$), respiratory rate (RR), positive end-expiratory pressure (PEEP), or the inspiratory oxygen concentration ($FiO_2$) made available by the ventilator, and a regulator unit, which is in communication with the measuring device and with the control device, wherein the measuring device is configured in such a way that it carries out a repeating measurement of the at least one patient-specific physiological parameter at time intervals, and wherein the regulator unit is configured in such a way that it carries out an adaptation of the at least one technical respiration parameter on the basis of the repeating measurement of the patient-specific physiological parameter.

13. The ventilator of item 12, wherein the at least one patient-specific physiological parameter corresponds to at least one of the parameters which comprise airway dead space ($V_{Daw}$), alveolar dead space ($V_{Dalv}$) or physiological dead space ($V_{Dphys}$) of the patient.

14. The ventilator of any one of items 12 or 13, wherein the measuring device furthermore is configured in such a way that it carries out the repeating measurement of the at least one patient-specific physiological parameter after each breath taken by the patient.

15. The ventilator of any one of items 12 through 14, wherein the measuring device is designed as a capnograph and is configured in such a way that it carries out the repeating measurement of the at least one patient-specific physiological parameter by capnography, preferably volumetric capnography, and wherein the at least one patient-specific physiological parameter corresponds to at least one parameter directly representing the $CO_2$ gas exchange in the lungs of the patient, preferably at least one of the parameters comprising end-expiratory $CO_2$ partial pressure in an exhaled gas mixture ($PETCO_2$), alveolar $CO_2$ partial pressure ($PACO_2$), or volume of $CO_2$ eliminated in a single breath by the patient ($VCO_2$).

16. The ventilator of any one of items 12 through 15, wherein the measuring device is configured in such a way that it carries out the repeating measurement of the at least one patient-specific physiological parameter by means of oxygraphy, preferably volumetric oxygraphy, and wherein the at least one patient-specific physiological parameter corresponds to at least one of the parameters which comprise alveolar $O_2$ partial pressure ($PCO_2$) and/or volume of oxygen taken up by the patient in one breath ($VO_2$).

17. The ventilator of any one of items 12 through 16, wherein the at least one patient-specific physiological parameter corresponds to at least the parameter arterial $CO_2$ partial pressure ($PaCO_2$), the measuring device being configured in such a way that it approximates the arterial $CO_2$ partial pressure ($PaCO_2$) via non-invasively measured patient-specific physiological parameters.

18. The ventilator of any one of items 12 through 17, wherein the measuring device is designed as a pulse oximeter and is configured in such a way that it carries out the repeating measurement of the at least one patient-specific physiological parameter by means of pulse oximetry, and wherein the at least one patient-specific physiological parameter corresponds at least to the parameter arterial oxygen saturation of the blood of the patient ($SpO_2$).

19. The ventilator of any one of items 12 through 18, wherein the measuring device is configured in such a way that, as the at least one patient-specific physiological parameter, it determines the parameter volumetric blood flow of the intrapulmonary right-to-left shunt of the patient ($PBF_{SHUNT}$) from the parameters comprising alveolar oxygen concentration, amount of oxygen taken up by the patient in one breath and/or arterial oxygen saturation of the blood of the patient ($SpO_2$).

20. The ventilator of any one of items 12 through 19, wherein the control device is configured in such a way that it carries out a recruiting maneuver at the start of the artificial ventilation, wherein lung overdistension is achieved by initial provision of an increased ventilation pressure, and then the ventilation pressure is reduced and a PEEP titration is carried out.

21. The ventilator of any one of items 12 through 20, wherein a monitoring unit is provided, which is configured in such a way that a ventilation pressure amplitude is permanently monitored during an artificial ventilation, an alarm being triggered if a preset maximum ventilation pressure amplitude is exceeded.

22. The ventilator of any one of items 12 through 21, wherein based on a recording of at least one patient-specific physiological parameter, the control unit determines proportions (in %) and/or absolute values (in ml) for regions of the lungs/the lung filling which, relative to at least the one patient-specific physiological parameter, represent anatomic dead space and/or represent alveolar dead space volume and/or represent functional alveoli and/or represent a shunt and/or represent VtCO2, the regions of the lungs being shown differently in a graph (by coloring or hatching) according to their proportions or absolute values and preferably being displayed in a graphic representation of the lungs.

What is claimed is:

1. A method for operating a ventilator for artificial ventilation of a patient, wherein the method comprises:

initial recording of at least one patient-specific physiological parameter, initial setting of at least one technical respiration parameter, and ventilation of the patient based on the at least one technical respiration parameter, wherein the at least one patient-specific physiological parameter is at least the parameter arterial $CO_2$ partial pressure ($PaCO_2$), approximated via non-invasively measured values of an alveolar partial pressure $PACO_2$ by determining an arterial-alveolar $CO_2$ difference Pa-$ACO_2$ and adding the difference to the non-invasively measured values of the alveolar partial pressure $PACO_2$, and wherein at least one technical respiration parameter corresponds to a positive end-expiratory pressure (PEEP), wherein a measurement of the at least one patient-specific physiological parameter is carried out by the ventilator after each breath of the patient, and wherein an adaptation of the at least one technical respiration parameter is effected by the ventilator on the basis of the measurement of the at least one patient-specific physiological parameter.

2. The method of claim 1, wherein at least one additional patient-specific physiological parameter is at least one of the parameters which comprise airway dead space ($V_{Daw}$), alveolar dead space ($V_{Dalv}$) or physiological dead space ($V_{Dphys}$) of the patient.

3. The method of claim 1, wherein the measurement of the at least one patient-specific physiological parameter is effected by capnography by the ventilator.

4. The method of claim 1, wherein measurement of at least one additional patient-specific physiological parameter is effected by oxygraphy, and wherein the at least one additional patient-specific physiological parameter corresponds to at least one of the parameters comprising alveolar $O_2$ partial pressure ($PAO_2$) and/or volume of oxygen taken up by the patient in one breath ($VO_2$).

5. The method of claim 1, wherein measurement of at least one additional patient-specific physiological parameter is effected by pulse oximetry, and wherein the at least one additional patient-specific physiological parameter corresponds to at least the parameter arterial oxygen saturation of blood of the patient ($SpO_2$).

6. The method of claim 1, wherein, as at least one additional patient-specific physiological parameter, the parameter volumetric blood flow of an intrapulmonary right-to-left shunt of the patient ($PBF_{SHUNT}$) is determined from the parameters which comprise alveolar oxygen concentration, amount of oxygen taken up by the patient in one breath and/or arterial oxygen saturation of blood of the patient ($SpO_2$).

7. The method of claim 1, wherein a recruiting maneuver is carried out at a start of an artificial ventilation, wherein lung overdistension is achieved by initial provision of an increased ventilation pressure, and then a ventilation pressure is reduced and a PEEP titration is carried out.

8. The method of claim 1, wherein a ventilation pressure amplitude is permanently monitored during artificial ventilation, an alarm being triggered if a preset maximum ventilation pressure amplitude is exceeded.

9. A ventilator for artificial ventilation of a patient, which ventilator comprises:

a measuring device configured to record at least one patient-specific physiological parameter, a control device configured to set at least one technical respiration parameter and carrying out the ventilation of the patient on the basis of the at least one technical respiration parameter, wherein the at least one patient-specific physiological parameter is at least the parameter arterial $CO_2$ partial pressure ($PaCO_2$), which is approximated via non-invasively measured values of an alveolar partial pressure $PACO_2$ by determining an arterial-alveolar $CO_2$ difference Pa-$ACO_2$ and adding the difference to the non-invasively measured values of the alveolar partial pressure $PACO_2$, and wherein the at least one technical respiration parameter corresponds to at least a positive end-expiratory pressure (PEEP), and a regulator unit, which is in communication with the measuring device and with the control device, wherein the measuring device is configured in such a way that it carries out a measurement of the at least one patient-specific physiological parameter after each breath taken by the patient, and wherein the regulator unit is configured in such a way that it carries out an adaptation of the at least one technical respiration parameter on the basis of the measurement of the at least one patient-specific physiological parameter.

10. The ventilator of claim 9, wherein the measuring device is designed as a capnograph and is configured in such a way that it carries out the measurement of the at least one patient-specific physiological parameter by capnography.

11. The ventilator of claim 10, wherein the ventilator further comprises an additional measuring device, wherein the additional measuring device is configured in such a way that it carries out measurement of at least one additional patient-specific physiological parameter by oxygraphy, and wherein the at least one additional patient-specific physiological parameter corresponds to at least one of the parameters which comprise alveolar $O_2$ partial pressure ($PAO_2$) and/or volume of oxygen taken up by the patient in one breath ($VO_2$).

12. The ventilator of claim 9, wherein the measuring device is additionally designed as a pulse oximeter and is configured in such a way that it carries out the measurement of at least one additional patient-specific physiological parameter by pulse oximetry, the at least one additional patient-specific physiological parameter corresponding at least to the parameter arterial oxygen saturation of blood of the patient ($SpO_2$).

13. The ventilator of claim 9, wherein the measuring device is configured in such a way that, as an additional patient-specific physiological parameter, it determines the parameter volumetric blood flow of an intrapulmonary right-to-left shunt of the patient ($PBF_{SHUNT}$) from the parameters comprising alveolar oxygen concentration, amount of oxygen taken up by the patient in one breath and/or arterial oxygen saturation of the blood of the patient ($SpO_2$).

14. The ventilator of claim 9, wherein the control device is configured in such a way that it carries out a recruiting maneuver at a start of the artificial ventilation, wherein lung overdistension is achieved by initial provision of an increased ventilation pressure, and then a ventilation pressure is reduced and a PEEP titration is carried out.

* * * * *